United States Patent [19]

Fouquet et al.

[11] 4,226,780

[45] Oct. 7, 1980

[54] MANUFACTURE OF PROPYLENE OXIDE

[75] Inventors: Gerd Fouquet, Ludwigshafen; Franz Merger, Frankenthal; Karl Baer, Weinheim, all of Fed. Rep. of Germany

[73] Assignee: BASF Aktiengesellschaft, Ludwigshafen, Fed. Rep. of Germany

[21] Appl. No.: 879,723

[22] Filed: Feb. 21, 1978

[30] Foreign Application Priority Data

Mar. 4, 1977 [DE] Fed. Rep. of Germany ....... 2709440

[51] Int. Cl.$^3$ .......................................... C07D 301/02
[52] U.S. Cl. ................................................ 260/348.16
[58] Field of Search ..................................... 260/348.16

[56] References Cited

U.S. PATENT DOCUMENTS

| | | | |
|---|---|---|---|
| Re. 29,597 | 3/1978 | Brownstein et al. | 260/348.16 |
| 4,012,424 | 3/1977 | Sherwin et al. | 260/348.32 |

*Primary Examiner*—Norma S. Milestone
*Attorney, Agent, or Firm*—Keil & Witherspoon

[57] ABSTRACT

Propylene oxide is prepared by elimination of water from propylene glycol which in turn is obtainable from propylene glycol acetate. The water is eliminated in the gas phase over a solid catalyst which consists of a weakly acidic carrier and an alkaline additive. The process offers a new method of manufacturing propylene oxide.

5 Claims, No Drawings

MANUFACTURE OF PROPYLENE OXIDE

The present invention relates to a process for the manufacture of propylene oxide by eliminating water from propylene glycol in the gas phase over a catalyst.

German Laid-Open Application DOS 2,412,136 discloses that alkylene oxides may advantageously be manufactured by catalytic deacyloxylation of vicinal hydroxy-ester compounds in the vapor phase over a solid basic compound. This process gives high yields. However, it suffers from the disadvantage that the concentration of propylene oxide in the material leaving the reactor is low, and that the carboxylic acid eliminated is difficult to separate off.

Propylene glycol has hitherto as a rule been manufactured from propylene oxide. At first sight it would therefore appear, to those skilled in the art, that to manufacture propylene oxide from propylene glycol is a circuitous approach. It is true that the conventional manufacture of propylene oxide by the chlorohydrin process proceeds with high yields, but the investment costs are very high and because of the formation of very large amounts of calcium chloride or sodium chloride this process entails substantial pollution of the environment. Furthermore, numerous patents (cited in more detail below) have in the interim disclosed processes which permit the acyloxylation of propylene to give propylene glycol esters, which can be hydrolyzed to give propylene glycol. Accordingly it would in principle be possible to obtain propylene glycol from propylene.

However, the conversion of propylene glycol to propylene oxide by a direct method, without an ester intermediate, and on a useful scale, has not previously been disclosed.

We have found, surprisingly, that propylene oxide is obtained with good selectivity and in high yield if 1,2-propylene glycol or a mixture which in addition to 1,2-propylene glycol contains one or more monoesters, with or without diesters, of 1,2-propylene glycol, is heated in the gas phase at from 300° to 500° C. under atmospheric pressure or, preferably, reduced pressure, over a solid catalyst which comprises a weakly acidic carrier and a basic alkali metal compound.

Propylene glycol is advantageously manufactured via its esters, obtained by acyloxylation of propylene. Preferred esters are the acetates, i.e. 1,2- or 2,1-hydroxyacetoxypropane and 1,2-diacetoxypropane.

The manufacture of these esters is described in detail in German Laid-Open Applications DOS Nos. 2,620,444, 2,636,669 and 2,636,670, French Patents 1,421,288 and 1,419,966 and U.S. Pat. Nos. 3,542,857 and 3,262,969.

The mixtures obtained as described in these patents may be hydrolyzed in the conventional manner using acidic catalysts, e.g. dilute sulfuric acid or acetic acid.

According to another, preferred embodiment the hydrolysis is carried out in the presence of an organic cation exchanger, containing sulfonic acid groups, suitably at from 50° to 150° C.

Examples of organic cation exchangers containing sulfonic acid groups are resins comprising sulfonated crosslinked styrene polymers such as sulfonated styrene/divinylbenzene copolymers or phenol-formaldehyde or benzene-formaldehyde resins containing sulfonic acid groups. The use of a sulfonated styrene/divinylbenzene copolymer as the exchange resin is preferred. The exchange resins are used in the acidic form, not as salts. The catalyst suitably has a particle size of from 10 to 2,000, preferably from 50 to 1,800, especially from 300 to 1,300, micrometers. Examples of suitable products are the exchange resins sold under the name of ®AMBERLITE IR-120, ®DOWEX 50, ®LEWATIT S-100, ®LEWATIT SC 102, ®LEWATIT SC 104, ®LEWATIT SPC 108, ®NALCITE HCR, ®PERMUTIT RS and ®WOFATIT KPS-200, as well as cation exchangers in powder form, e.g. ®LEWASORB A 10.

As a rule, exchangers of normal coarse-grained consistency are employed, so that the reaction may be carried out either in suspension or in a fixed bed. Where a fixed catalyst is used it is necessary to ensure that the water required for hydrolysis is not withdrawn from the hydrolysis reaction by phase separation. Compared to mineral acids or carboxylic acids (e.g. acetic acid) as catalysts, cation exchangers offer substantial advantages, since they catalyze the hydrolysis at a high speed at substantially lower temperatures, especially below 110° C., and/or they can be separated off in a simple manner and hence do not cause the formation of by-products during hydrolysis or later in the process. Furthermore, this method permits reaction at atmospheric pressure or only slightly elevated pressure.

Any unreacted water, and the acetic acid formed, are isolated from the reaction mixture, for example by distillation, after removing the ion exchanger, or are distilled off during the reaction, and the acetic acid is returned to the acetoxylation stage.

According to a particularly preferred embodiment, the propylene glycol acetates are reacted with an alcohol, especially with methanol, to give propylene glycol and methyl acetate. The catalysts used are cation exchangers of normal coarse-grained consistency or of milled consistency, so that the reaction may be carried out either in suspension or in a fixed bed. Preferably, the solvolysis is carried out in suspension whilst simultaneously distilling off the azeotropic mixture of methanol and methyl acetate, since in this way the reaction equilibrium can be shifted substantially toward the reaction products. The methyl acetate formed can, in contrast to acetic acid, be removed very easily. In addition it is possible to acetoxylate propylene in the presence of methyl acetate instead of acetic acid, without a separate hydrolysis of the methyl acetate, by adding the requisite amount of water to the methyl acetate and carrying out the acetoxylation in the presence of a hydrolysis catalyst. Details mentioned above may be found in German Laid-Open Application DOS No. 2,623,562.

The hydrolysis or solvolysis need not necessarily be taken to complete conversion of the propylene glycol acylates to propylene glycol. Instead, it is possible to use a less than stoichiometric amount of water or methanol to produce a mixture of propylene glycol with propylene glycol monoacetate, which may even contain some of the diacetate, which mixture, after removal of the unreacted water or methanol and of the acetic acid and/or methyl acetate, is subjected to the catalytic gas phase reaction in accordance with the invention, since propylene glycol monoacetate is also converted to propylene oxide over the catalysts to be used according to the invention. Equally, some of the propylene glycol diacetate is similarly converted, since, under the reaction conditions, the diacetate and propylene glycol give the monoacetate, which in turn reacts further. In addition, the water formed during the conversion of propylene glycol to propylene oxide is able to hydrolyze some proportion of the acetates.

Advantageously, however, the solvolysis is taken to a point where at least all the diacetate has been converted.

Accordingly, preferred mixtures for carrying out the reaction according to the invention contain from 0 to 30 mole% of propylene glycol monoacetates and from 100 to 70 mole% of propylene glycol.

On partial hydrolysis of the mixtures obtained by acetoxylation, the product may however contain substantially more monoacetate, for example up to 55 mole%, and substantial amounts of diacetate, for example up to 35 mole%, in addition to propylene glycol, the proportion of which may be as low as 10%.

However, mixtures with propylene glycol as the essential constituent are preferred.

The catalyst to be used according to the invention should contain weakly acidic and basic components, preferably a weakly acidic carrier which is thermally and mechanically stable under the reaction conditions and is modified with a basic component.

Examples of suitable weakly acidic components are titanium dioxide, zirconium dioxide and especially silica. The latter may, for example, be in the form of cristobalite. A particularly suitable acidic "carrier" comprises a precipitated silica which is obtained by reacting a dilute waterglass, to which monoacidic bases have been added, with dilute sulfuric acid. The resulting precipitate is washed, dried, extruded and heated under conditions such that the extrudates obtained have a porosity of from 0.4 to 1.3, preferably from 0.6 to 1.0, cc/g. Their surface area (measured by the BET method) is from 50 to 200 m$^2$/g, preferably from 100 to 150 m$^2$/g. The crystal structure of the carrier may be amorphous, but cristobalite may also be detectable in the X-ray diagram.

An alkali metal compound, especially a potassium compound, in an amount of from 5 to 25% by weight, preferably from 8 to 15% by weight, is applied to this carrier. Examples of suitable alkali metal compounds are, in particular, the low-molecular weight carboxylates, preferably the acetates (as well as compounds which may form alkali metal carboxylates with carboxylic acids under the reaction conditions).

The catalyst composition, i.e. the alkali metal compound, may be applied to the carrier by impregnation but may also be worked into the composition to be molded.

The reaction may be carried out over a fixed catalyst or in a fluidized bed.

The reaction is advantageously carried out by spraying the starting mixtures into the reaction zone, heated to the reaction temperature, and bringing them into contact with the catalyst for a brief residence time, e.g. from 1 to 0.0004 minute, preferably from 10 to 0.1 seconds.

The reaction temperature is as a rule from 200° to 500° C., preferably from 300° to 450° C.

Though the reaction according to the invention may also be carried out under atmospheric pressure, the use of reduced pressure, e.g. down to 0.01 bar, preferably from 0.15 to 0.5 bar, is preferred. What matters is not the absolute pressure of the system but the partial pressure of the said reactive components, so that when working under atmospheric pressure dilution with an inert gas, e.g. nitrogen, has the same effect as reducing the pressure.

Even at relatively high conversions, e.g. at about 30% conversion, the new process exhibits very good selectivity of more than 75%, based on propylene oxide, and more than 90%, based on propylene oxide and further useful products, e.g. propionaldehyde and acetone. As a result, a high space-time yield (for example about 500 g/l . h) is achievable and the material leaving the reactor contains a substantially increased percentage of propylene oxide, so that working up to give propylene oxide becomes simpler.

Accordingly, the new process offers a new method for the economical manufacture of propylene oxide without substantial pollution of *the* environment.

EXAMPLE 1

A suspension of 800 parts of 1,2-diacetoxypropane, 960 parts of methanol and 176 part of cation exchanger (®Lewatit SC 102) is prepared in a stirred reactor, provided with a distillation unit, by stirring at 300 rpm, and the mixture is heated at 65° C.; the exchange resin is a sulfonated styrene/divinylbenzene copolymer resin, and has a gel-like structure and a particle size of from 0.3 to 1.2 mm). In the course of 30 minutes, 158 parts of the azeotropic mixture of methanol and methyl acetate, boiling at 54° C., are distilled off. The ion exchanger is then filtered off. Fractional distillation gives 1,180 parts of methanol + methyl acetate and 407 parts of a product mixture which, according to analysis by gas chromatography, contains 330 parts of 1,2-propanediol and 77 parts of 1-acetoxy-2-hydroxy-propane and 1-hydroxy-2-acetoxy-propane (boiling point 75°–80° C./12 mm Hg).

EXAMPLE 2

A suspension is prepared from 1,600 parts of 1,2-diacetoxypropane, 1,080 parts of water and 270 g of cation exchanger (®Lewatit SC 102) in a stirred reactor, provided with a distillation unit, by stirring at 300 rpm, and the mixture is heated at 105° C. 240 parts of a mixture of water and acetic acid are distilled off in the course of 20 minutes and the ion exchanger is then filtered off. Fractional distillation gives 1,490 parts of an acetic acid/water mixture and 958 parts of a product mixture which, according to analysis by gas chromatography, contains 136 parts of 1,2-diacetoxy-propane, 355 parts of 1,2-propanediol and 467 parts of 1-hydroxy-2-acetoxy-propane and 1-acetoxy-2-hydroxypropane (boiling point 75°–80° C./12 mm Hg).

EXAMPLE 3

A suspension is prepared from 800 parts of 1,2-diacetoxypropane, 540 parts of water and 135 g of cation exchanger (®Amberlite IR 120) in a stirred reactor by stirring at 300 rpm, and the mixture is heated at 100° C. (The exchange resin is a sulfonated styrene/divinylbenzene copolymer resin; it has a gel-like structure and a particle size of from 0.3 to 1.2 mm). After 1 hour, the ion exchanger is filtered off. Fractional distillation gives 890 parts of an acetic acid/water mixture and 550 parts of a product mixture which according to analysis by gas chromatography contains 188.7 parts of 1,2-diacetoxypropane, 199.3 parts of 1-acetoxy-2-hydroxy-propane and 2-hydroxy-1-acetoxy-propane, and 162.0 parts of 1,2-propanediol, and has a boiling point 75°–80° C./12 mm Hg.

EXAMPLE 4

A suspension is prepared from 400 parts of 1,2-diacetoxypropane, 480 parts of methanol and 88 parts of cation exchanger (®Lewatit SC 104) in a stirred reactor, provided with a distillation unit, by stirring at 300 rpm, and the mixture is heated at 65° C. (the exchange resin is a sulfonated styrene/divinylbenzene copolymer resin; it has a gel-like structure and a particle size of from 0.3 to 1.2 mm). 59 parts of the azeotropic mixture of methanol and methyl acetate, of boiling point 54° C., are distilled off in the course of 15 minutes and the ion exchanger is then filtered off. Fractional distillation gives 602 parts of a methanol/methyl acetate mixture and 219 parts of a product mixture which according to analysis by gas chromatography contains 136 parts of 1,2-propanediol and 83 parts of 1-acetoxy-2-hydroxypropane and 1-hydroxy-2-acetoxypropane (boiling point 75°–80° C./12 mm Hg).

EXAMPLE 5

A suspension is prepared from 800 parts of 1,2-diacetoxypropane, 960 parts of methanol and 176 parts of cation exchanger (®Lewatit SPC 108) in a stirred reactor, provided with a distillation unit, by stirring at 300 rpm, and the mixture is heated at 62° C. (The exchange resin is a sulfonated styrene/divinylbenzene copolymer resin; it has a macro-porous structure and a particle size of from 0.3 to 15 mm). 910 parts of the azeotropic mixture of methanol and methyl acetate, of boiling point 54° C., are distilled off in the course of 4 hours. The ion exchanger is then filtered off. Distillation gives 470 parts of a methyl acetate/methanol mixture and 376 parts of 1,2-propanediol.

EXAMPLE 6

200 ml of silica (particle size 2–3 mm) charged with 10% of potassium acetate are filled into a tubular reactor equipped with a vaporizer. The reactor is heated at 400° C. and is fed with 10 parts of 1,2-propanediol per minute under a pressure of 160 mm. After 100 minutes' operation, the material which has left the reactor is analyzed by gas chromatography and subjected to fractional distillation. The yield (according to the analysis) is 156.1 parts (75% of theory) of propylene oxide of boiling point 34°–35° C, and 34.2 parts (16.4% of theory) of propionaldehyde of boiling point 49°–50° C.

EXAMPLE 7

200 ml of silica (particle size 2–3 mm) charged with 10% of potassium acetate are filled into a tubular reactor equipped with a vaporizer. The reactor is heated at 350° C. and fed with 4 parts of 1,2-propanediol per minute. After 100 minutes' operation, the material which has left the reactor is analyzed by gas chromatography and subjected to fractional distillation. The yield (according to the analysis) is 59.2 parts (81.5% of theory) of propylene oxide of boiling point 34°–35° C. and 9.5 parts (13.0% of theory) of propionaldehyde of boiling point 49°–50° C.

EXAMPLE 8

200 ml of silica (particle size 2–3 mm) charged with 15% of potassium acetate are filled into a tubular reactor equipped with a vaporizer. The reactor is heated at 410° C. and is fed with 10 parts per minute of a reaction mixture, consisting of 3.4 parts of 1,2-diacetoxy-propane, 3.6 parts of 1-acetoxy-2-hydroxypropane and 1-hydroxy-2-acetoxy-propane and 3.0 parts of 1,2-propanediol, under a pressure of 160 mm. After 100 minutes' operation, the material leaving the reactor is analyzed by gas chromatography and subjected to fractional distillation. The yield (analysis) is 88.2 parts of propylene oxide (74.2% of theory) of boiling point 34°–35° C. and 17.5 parts of propionaldehyde (14.7% of theory) of boiling point 49°–50° C.

EXAMPLE 9

200 ml of silica (particle size 2–3 mm) charged with 10% of potassium acetate are filled into a tubular reactor equipped with a vaporizer. The reactor is heated at 400° C. and is fed with 8 parts per minute of a reaction mixture which consists of 5.0 parts of 1,2-propanediol and 3.0 parts of 1-acetoxy-2-hydroxypropane and 1-hydroxy-propane under a pressure of 180 mm. After 100 minutes' operation, the material which has left the reactor is analyzed by gas chromatography and subjected to fractional distillation. The yield (analysis) is 92.2 parts (76.8% of theory) of propylene oxide of boiling point 34°–35° C. and 14.6 parts of propionaldehyde (12.2% of theory) of boiling point 49°–50° C.

We claim:

1. A process for the manufacture of propylene oxide which comprises heating 1,2-propylene glycol or a mixture containing at least 70% by weight of 1,2-propylene glycol and up to 30% by weight of one or more monoesters, with or without diesters, of 1,2-propylene glycol with low molecular weight carboxylic acids, in the gas phase at a temperature of from 300° to 500° C. under a pressure of from 0.01 to 1 bar over a catalyst which contains a weakly acidic carrier and an added basic alkali metal salt of a low-molecular weight carboxylic acid.

2. A process as set forth in claim 1, wherein the catalyst used contains silica as the weakly acidic carrier, together with from 5 to 25% by weight of an alkali metal salt of a low-molecular weight carboxylic acid.

3. A process as set forth in claim 1, wherein the starting material used is a mixture which is obtained by reacting a mixture, obtained by acetoxylation of propylene, of 1,2-propylene glycol diacetate and 1,2-propylene glycol monoacetate with a low-molecular weight alcohol, with complete conversion to 1,2-propylene glycol or partial conversion to a mixture containing at least 70% by weight of 1,2-propylene glycol and the acetate of the low-molecular weight alcohol, removing the said acetate and recycling it to the acetoxylation stage.

4. A process as set forth in claim 3, wherein the low-molecular weight alcohol used is methanol.

5. A process as set forth in claim 1, wherein the starting material used is a mixture which is obtained by acetoxylating propylene, hydrolyzing the acetate with water in the presence of an acidic organic ion exchanger containing sulfonic acid groups, and isolating the mixed hydrolysis products.

* * * * *